(12) United States Patent
Lee et al.

(10) Patent No.: US 11,692,987 B2
(45) Date of Patent: Jul. 4, 2023

(54) COCR₂O₄-BASED GAS SENSOR AND METHOD FOR MANUFACTURING THE SAME

(71) Applicant: Korea University Research and Business Foundation, Seoul (KR)

(72) Inventors: Jongheun Lee, Seoul (KR); Boyoung Kim, Seoul (KR); Jiwook Yoon, Seoul (KR); Kunho Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 618 days.

(21) Appl. No.: 16/718,659

(22) Filed: Dec. 18, 2019

(65) Prior Publication Data

US 2020/0209206 A1 Jul. 2, 2020

(30) Foreign Application Priority Data

Dec. 28, 2018 (KR) .......................... 10-2018-0171659

(51) Int. Cl.
| | |
|---|---|
| *G01N 33/00* | (2006.01) |
| *B22F 5/10* | (2006.01) |
| *B22F 3/24* | (2006.01) |
| *B22F 7/02* | (2006.01) |
| *B22F 1/10* | (2022.01) |
| *B22F 1/142* | (2022.01) |

(52) U.S. Cl.
CPC .......... *G01N 33/0047* (2013.01); *B22F 1/10* (2022.01); *B22F 1/142* (2022.01); *B22F 3/24* (2013.01); *B22F 5/10* (2013.01); *B22F 7/02* (2013.01); *B22F 2003/242* (2013.01); *B22F 2302/25* (2013.01)

(58) Field of Classification Search
CPC .......... G01N 33/0047; G01N 33/0036; G01N 33/0037; G01N 33/0039; G01N 33/004; G01N 33/005; B22F 1/142; B22F 1/10; B22F 3/24; B22F 5/10; B22F 7/02; B22F 2003/242; B22F 2302/25
See application file for complete search history.

(56) References Cited

FOREIGN PATENT DOCUMENTS

| EP | 3260855 A1 * | 12/2017 | ............. B82B 1/008 |
|---|---|---|---|
| JP | 6224311 B2 | 11/2017 | |
| KR | 10-0325344 B1 | 5/2002 | |
| KR | 10-1246529 B1 | 3/2013 | |

(Continued)

OTHER PUBLICATIONS

"Highly selective and sensitive xylene sensors using Cr2O3-ZnCr2O4 hetero-nanostructures prepared by galvanic replacement." Sensors and Actuators B: Chemical 235 (2016): 498-506.) (Year: 2016).*

(Continued)

*Primary Examiner* — Anthony J Zimmer
*Assistant Examiner* — Ricardo D Morales
(74) *Attorney, Agent, or Firm* — NSIP Law

(57) ABSTRACT

A method of manufacturing a gas sensor for detecting xylene is provided. A method of manufacturing a gas sensor includes reacting a mixed material including a first material containing a cobalt (Co) element and a second material containing a chromium (Cr) element to form a $CoCr_2O_4$ hollow structure having a hollow shape.

3 Claims, 10 Drawing Sheets

(56) References Cited

FOREIGN PATENT DOCUMENTS

| KR | 10-1303616 | B1 | 9/2013 | |
|---|---|---|---|---|
| KR | 10-2014-0018573 | A | 2/2014 | |
| KR | 10-2014-0125897 | A | 10/2014 | |
| KR | 10-1491819 | B1 | 2/2015 | |
| KR | 10-2015-0085560 | A | 7/2015 | |
| KR | 10-1550356 | B1 | 9/2015 | |
| KR | 10-1616173 | B1 | 5/2016 | |
| KR | 10-1764487 | B1 | 8/2017 | |
| KR | 10-2017-0137619 | A | 12/2017 | |
| KR | 10-1806742 | B1 | 1/2018 | |
| KR | 10-1813226 | B1 | 1/2018 | |
| WO | WO-2017022992 | A1 * | 2/2017 | ............... B82B 1/00 |

OTHER PUBLICATIONS

Kim et al. "Hollow spheres of CoCr 2 O 4-Cr 2 O 3 mixed oxides with nanoscale heterojunctions for exclusive detection of indoor xylene." Journal of Materials Chemistry C 6.40 (2018): 10767-10774. (Year: 2018).*

WO-2017022992-A1 english (Year: 2017).*

Kim, Dae-Chul et al., "Application of Spinel-Type Cobalt Chromite as a Novel Catalyst for Combustion of Chlorinated Organic Pollutants", *Environmental Science & Technology*, vol. 35, No. 1, 2001 (pp. 222-226).

Fleischer, Maximilian et al., "Selective gas detection with high-temperature operated metal oxides using catalytic filters", *Sensors and Actuators B: Chemical*, vol. 69, Issues 1-2, Sep. 10, 2000, (pp. 205-210).

Pirogova, G. N. et al., "Catalytic properties of chromites with a spinel structure in the oxidation of CO and hydrocarbons and reduction of nitrogen oxides", Russian Chemical Bulletin, vol. 50, Issue 12, Dec. 2001 (pp. 2377-2380).

Cabot, A. et al., "Mesoporous catalytic filters for semiconductor gas sensors", *Thin Solid Films*, vol. 436, Issue 1, Jul. 22, 2003, (pp. 64-69).

Fino, D. et al., "Catalytic removal of NOx and diesel soot over nanostructured spinel-type oxides", *Journal of Catalysis*, vol. 242, Issue 1, Aug. 15, 2006, (pp. 38-47).

Kim, Hyo-Joong et al., "Enhanced ethanol sensing characteristics of In2O3-decorated NiO hollow nanostructures via modulation of hole accumulation layers", *ACS Applied Materials and Interfaces*, vol. 6, Issue 20, Jan. 1, 2014 (pp. 18197-18204).

Jeong, Hyun-Mook et al., "Cr-doped Co3O4 nanorods as chemiresistor for ultraselective monitoring of methyl benzene", *Sensors and Actuators B: Chemical*, vol. 201, Oct. 1, 2014, (pp. 482-489).

Qu, Fengdong et al., "Preparation and Xylene-Sensing Properties of Co3O4 Nanofibers", *International Journal of Applied Ceramic Technology*, vol. 11, Issue 4, Jul./Aug. 2014 (pp. 619-625).

Hwang, Su-Jin et al., "Pure and Palladium-Loaded Co3O4 Hollow Hierarchical Nanostructures with Giant and Ultraselective Chemiresistivity to Xylene and Toluene", Chemistry A European Journal, vol. 21, Issue 15, Apr. 7, 2015 (pp. 5872-5878).

Lee, Chui-Soon et al., "Monolayer Co3O4 Inverse Opals as Multifunctional Sensors for Volatile Organic Compounds", *Chemistry—A European Journal*, vol. 22, Issue 21, May 17, 2016 (pp. 7102-7107).

Kim, Jae-Hyeok et al., "Highly selective and sensitive xylene sensors using Cr2O3-ZnCr2O4 hetero-nanostructures prepared by galvanic replacement", *Sensors and Actuators B: Chemical*, vol. 235, Nov. 1, 2016, (pp. 498-506).

Kim, Bo-Young et al., "Highly Selective Xylene Sensor Based on NiO/NiMoO4 Nanocomposite Hierarchical Spheres for Indoor Air Monitoring", *ACS Applied Materials and Interfaces*, vol. 8, Issue 50, Dec. 21, 2016 (pp. 34603-34611).

Georgescu, Vasile et al., "Complete oxidation of toluene on Co-Cr mixed oxide catalyst", *Revista De Chimie*, vol. 67, Issue 11, 2016 (pp. 2258-2261).

Li, Feng et al., "Xylene gas sensor based on Au-loaded WO3•H2O nanocubes with enhanced sensing performance", *Sensors and Actuators B: Chemical*, vol. 238, Jan. 2017, (pp. 364-373).

Zhang, Jiajun et al., "Facile synthesis of mesoporous hierarchical Co3O4—TiO2 p—n heterojunctions with greatly enhanced gas sensing performance", *Journal of Materials Chemistry A*, vol. 5, Issue 21, 2017 (pp. 10387-10397).

Zhang, Bingxue et al., "Facile synthesis of mesoporous Co3O4 nanofans as gas sensing materials for selective detection of xylene vapor", *Materials Letters*, vol. 218, May 1, 2018, (pp. 127-130).

Jo, Young-Moo et al., "Metal-Organic Framework-Derived Hollow Hierarchical Co3O4 Nanocages with Tunable Size and Morphology: Ultrasensitive and Highly Selective Detection of Methylbenzenes", *ACS applied materials & interfaces*, vol. 10, Issue 10, 2018 (pp. 8860-8868).

Kim et al., "Hollow spheres of $CoCr_2O_4$—$Cr_2O_3$ mixed oxides with nanoscale heterojunctions for exclusive detection of indoor xylene," Journal of Materials Chemistry C, Sep. 21, 2018, pp. 10767-10774.

* cited by examiner

$CoCr_2O_4$-BASED GAS SENSOR AND METHOD FOR MANUFACTURING THE SAME

CROSS-REFERENCE TO RELATED APPLICATIONS

A claim for priority under 35 U.S.C. § 119 is made to Korean Patent Application No. 10-2018-0171659 filed on Dec. 28, 2018, in the Korean Intellectual Property Office, the entire contents of which are hereby incorporated by reference.

BACKGROUND

Embodiments of the inventive concept described herein relate to a gas sensor for detecting xylene and a method of manufacturing a gas sensor.

As having excellent gas sensitivity and economical price, a semiconductor type gas sensor using oxide is portable and miniaturized to be mounted on mobile and small devices and is advantageous to use where space is highly limited, such as a narrow indoor environment. In addition, the semiconductor type gas sensor may be widely used in various applications such as industrial gas detection, driver drunkness measurement, food freshness measurement of a refrigerator, and environmental monitoring in a vehicle or indoors. Recently, as an industry becomes high-tech and interest in human health and environmental pollution increases, there is a demand for high-performance gas sensitive materials to be used for an indoor and outdoor environmental gas detection sensor, a self-diagnostic gas sensor for diseases, and a high-performance artificial olfactory sensor which is capable of being mounted on a mobile device. In particular, there is a need for an indoor pollution measuring sensor capable of precisely monitoring environmental gases, which are generated in a room such as a living space and an office space where many people have been active for a long time in their daily lives.

In particular, a volatile organic compound which is one of gases necessary to be detected is harmful to a human body and is difficult to grasp its existence because the volatile organic compound is colorless and odorless and exists as gases at room temperature. The volatile organic compound such as benzene, xylene, toluene, formaldehyde, and alcohol is continuously generated in furniture, paints, organic solvents, paints, leather products, finishes, and the like, and it is known that it is difficult to detect the volatile organic compound with high sensitivity using the oxide semiconductor gas sensor because the volatile organic compound has a chemically stable macromolecular structure. The volatile organic compound may cause various fatal diseases such as headache, dizziness, eye disease, skin disease, and cancer when the volatile organic compound is exposed to the human body for a long time. Therefore, a gas sensitive material capable of detecting the volatile organic compound with high sensitivity is very important. Most oxide semiconductor gas sensors have a problem in that they exhibit similar sensitivity to the above-described gases or exhibit high reactivity to alcohol and formaldehyde, which frequently occur in indoor environments. However, the recommended lowest concentration limit for each volatile organic compound is different. Furthermore, benzene is known to be a carcinogen and xylene and toluene may cause various diseases of the respiratory and nervous systems. Therefore, there is a need for a gas sensor having selective sensitivity because each gas has a different effect on the human body and a manifested disease, as described above.

Many methods have been proposed to produce a gas sensitive material capable of being selectively detected by adding and applying a catalyst such as a heterooxide, a noble metal, and the like, having excellent catalyst activation to a specific gas, to an oxide semiconductor. Additional processes have been proposed, such as attachment of a specific gas filter to a gas sensor for increasing selectivity. However, these methods have a problem in that a degree of activation of single gas selectivity is insignificant or an additional cost for the process addition is increased and optimization and quantification of the catalyst is difficult. In particular, when selectivity to a hindered gas through the above methods is imparted, selective detection between gases having a benzene ring and having a similar molecular structure, such as xylene, toluene and benzene, is difficult.

SUMMARY

Embodiments of the inventive concept provide a gas sensor having high selectivity and high sensitivity to xylene and a method of manufacturing the gas sensor.

The problem to be solved by the inventive concept is not limited thereto, and other problems not mentioned will be clearly understood by those skilled in the art from the following description.

According to an exemplary embodiment, a method of manufacturing a gas sensor for detecting xylene includes reacting a mixed material including a first material containing a cobalt (Co) element and a second material containing a chromium (Cr) element to form a $CoCr_2O_4$ hollow structure having a hollow shape.

The mixed material may further include citric acid.

The first material and the second material may be provided to the mixed material to be a molar ratio between the cobalt element and the chromium element of 1:2 to 1:4.

The mixed material may further include a noble metal catalyst and the noble metal catalyst may include Pt, Pd, or Au.

The first material may include cobalt (II) nitrate hexahydrate ($Co(NO_3)_2 \cdot 6H_2O$) and the second material may include chromium (III) nitrate nonahydrate ($Cr(NO_3)_3 \cdot 9H_2O$).

The forming the hollow structure may include dissolving the mixed material in distilled water to prepare a spray solution; spraying the spray solution and heating the sprayed spray solution to form a $CoCr_2O_4$ precursor; and performing heat treatment of the $CoCr_2O_4$ precursor.

The method may further include coating the $CoCr_2O_4$ hollow structure prepared in the forming of the hollow structure on an insulator substrate where an electrode is provided.

According to an exemplary embodiment, a gas sensor includes a sensitive layer sensitive to xylene wherein the sensitive layer includes a $CoCr_2O_4$ hollow structure.

The sensitive layer may further include $Cr_2O_3$.

The sensitive layer may further include a noble metal catalyst.

The gas sensor may further include an insulator substrate formed of an insulator material; and an electrode connected to the insulator substrate, wherein the sensitive layer may be coated on the insulator substrate, and the electrode may be connected between the insulator substrate and the sensitive layer.

The gas sensor may further include a heater heating the sensitive layer.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
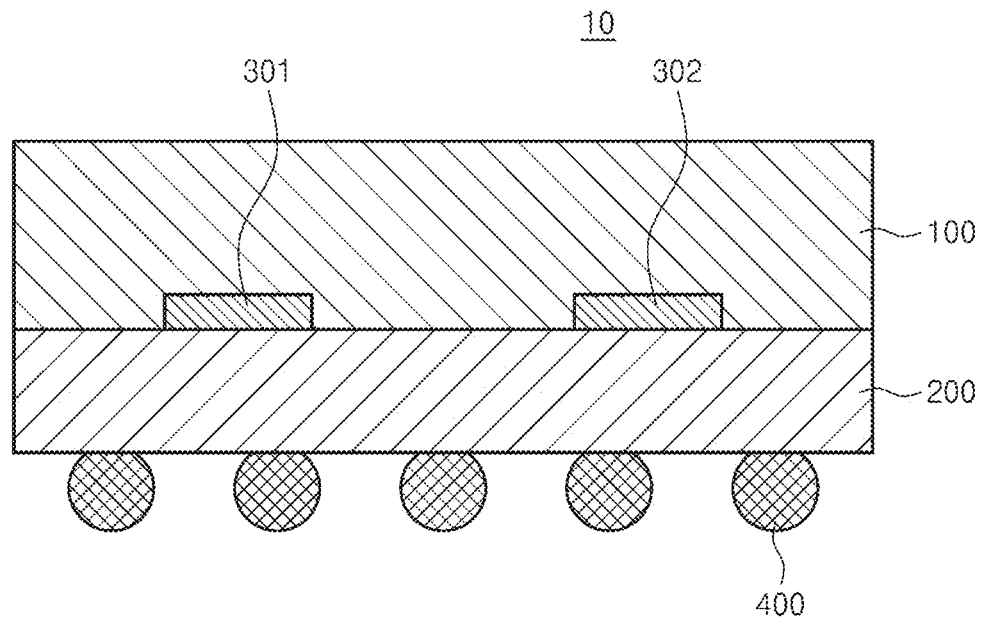
FIG. 1 is a cross-sectional view illustrating a gas sensor according to an embodiment of the inventive concept.

Hereinafter, an embodiment of the inventive concept will be described in more detail with reference to the accompanying drawings. The embodiments of the inventive concept may be modified in various forms, and the scope of the inventive concept should not be construed as being limited to the following embodiments. This embodiment is provided to more completely explain the inventive concept to those skilled in the art. Therefore, the shape of the elements in the drawings is exaggerated to emphasize a more clear description.

The inventive concept provides a highly sensitive and selective oxide semiconductor gas sensor having a high selectivity to xylene using pure $CoCr_2O_4$ while having a very low gas sensitivity to a hindered gas such as benzene, formaldehyde, alcohol, and the like. In addition, the inventive concept may provide a gas sensor where various catalysts (Pt, Au, or the like) are added to increase the sensitivity and selectivity to xylene through a synergistic effect of the catalysts and $CoCr_2O_4$.

FIG. 1 is a cross-sectional view illustrating a gas sensor 10 according to an embodiment of the inventive concept. Referring to FIG. 1, the gas sensor 10 includes a sensitive layer 100, an insulator substrate 200, electrodes 301 and 302, and a heater 400. The gas sensor 10 detects xylene.

The sensitive layer 100 is sensitive to xylene. For example, when the sensitive layer 100 is in contact with xylene, an electrical resistance changes. The sensitive layer 100 includes a $CoCr_2O_4$ hollow structure. According to an embodiment, the sensitive layer 100 may further include $Cr_2O_3$. Alternatively, the sensitive layer 100 may further include a noble metal catalyst. For example, Pt, Pd, Au, or Rh may be provided as the noble metal catalyst.

The insulator substrate 200 is provided to electrically connect the electrodes 301 and 302 to the sensitive layer 100. The insulator substrate 200 is provided as an insulator. For example, alumina (Al2O3) may be provided as the insulator substrate 200.

The electrodes 301 and 302 are connected to a top surface of the insulator substrate 200. The sensitive layer 100 is coated on the insulator substrate 200 whose the top surface is connected to the electrodes 301 and 302. Accordingly, the electrodes 301 and 302 are connected between the insulator substrate 200 and the sensitive layer 100. A resistance measuring device for measuring an electrical resistance is connected to the electrodes 301 and 302 which are connected to the insulator substrate 200 and the sensitive layer 100. When the sensitive layer 100 is in contact with xylene, the electrical resistance of the sensitive layer 100 may be changed and the changed electrical resistance of the sensitive layer 100 may be measured by the resistance measuring device to detect xylene.

The heater 400 heats the sensitive layer 100 to a temperature at which the sensitive layer 100 is activated for detection of xylene. According to an embodiment, the heater 400 may be provided on a bottom surface of the insulator substrate 200. The heater 400 may include a heating wire which generates heat by the electrical resistance. According to an embodiment, the heater 400 may heat the sensitive layer 100 to 250 to 350° C.

Hereinafter, a method of manufacturing a gas sensor according to an embodiment of the inventive concept will be described. The gas sensor 10 of FIG. 1 is an example of a gas sensor manufactured by the method of manufacturing the gas sensor according to an embodiment of the inventive concept.

Pure $Co_3O_4$ (Comparative Example 1-1) and pure $Cr_2O_3$ (Comparative Example 1-2) were synthesized using a spray pyrolysis method as Comparative Examples for Examples of the inventive concept. Pure $CoCr_2O_4$ sensitive materials (Example 1-1, Example 2-1) were synthesized through adjusting addition of precursors of Co and Cr using the same method. It was confirmed that pure $CoCr_2O_4$ had a composition advantages for xylene gas sensitization through experimental data presented below, unlike pure $Co_3O_4$ and pure $Cr_2O_3$.

In addition, the $CoCr_2O_4$ sensitive materials (Example 1-2, Example 1-3) which were produced with $Cr_2O_3$ in the same manner and $CoCr_2O_4$ sensitive materials added with Pt, Pd, or Au (Examples 2-2, 2-3, 2-4) were synthesized and gas sensitive properties were checked. In particular, the addition of the Pt catalyst greatly improved sensitivity to xylene, while lowering sensitivity to indoor environmental gases such as benzene, ethanol, formaldehyde, carbon monoxide, and the like, thereby increasing the detection selectivity of xylene. Accordingly, the embodiment of the inventive concept for sensitively and selectively detecting the specific gas is not limited to a manufacturing method having only $CoCr_2O_4$ content, includes a nanocomposite and a solid mixture containing Cr and Co of various compositions, and includes the sensitive material in which a noble metal catalyst, such as Pd or Au, is added to $CoCr_2O_4$.

In the inventive concept, pure $Co_3O_4$ (Comparative Example 1-1), pure $Cr_2O_3$ (Comparative Example 1-2), pure $CoCr_2O_4$ (Example 1-1, Example 2-1) and $Cr_2O_3$—$CoCr_2O_4$ (Example 1-2, Example 1-3), Pt—$CoCr_2O_4$ (Example 2-2), Pd—$CoCr_2O_4$ (Example 2-3), Au—$CoCr_2O_4$ (Example 2-4) were synthesized using the spray pyrolysis method to manufacture gas sensors, respectively. After manufacturing each gas sensor using each prepared sensitive material, the gas sensitivity of ethanol, xylene, toluene and the like were compared. In addition, the selectivity of xylene relative to ethanol was measured for all the Comparative Examples and Examples and the lowest limits of xylene detection of Examples 1-2 and Example 2-2 were measured.

As described above, a catalytic reaction between $CoCr_2O_4$ and $Cr_2O_3$, which are effective for decomposition of xylene, and Pt reduces the gas sensitivity of the oxide semiconductor gas sensor to ethanol or formaldehyde, which is highly reactive while the gas sensitivity to xylene known for being weak reactivity is significantly increased to be capable of selectively sensitive to xylene, i.e., an indoor environmental gas.

Figure 2:
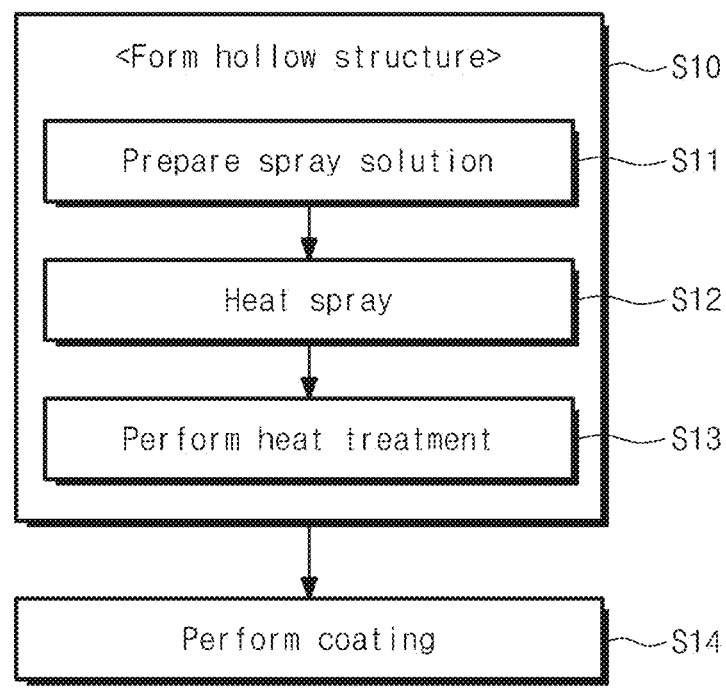
FIG. 2 is a flow chart illustrating a method of manufacturing a gas sensor according to an embodiment of the inventive concept.

FIG. 2 is a flow chart illustrating a method of manufacturing a gas sensor according to an embodiment of the inventive concept. Referring to FIGS. 1 and 2, a method of manufacturing a gas sensor according to an embodiment of the inventive concept manufactures a gas sensor for detecting xylene. The method of manufacturing the gas sensor includes forming a hollow structure in S10 and performing coating in S14.

In the forming of the hollow structure in S10, a mixed material including a first material containing a cobalt (Co) element, a second material containing a chromium (Cr) element, and citric acid is reacted to form the $CoCr_2O_4$ hollow structure to have a hollow shape.

The first material and the second material are provided to the mixed material such that a molar ratio between the cobalt element and the chromium element is 1:2 to 1:4. According to an embodiment, cobalt (II) nitrate hexahydrate $(Co(NO_3)_2 \cdot 6H_2O)$ may be provided as the first material and chromium (III) nitrate nonahydrate $(Cr(NO_3)_3 \cdot 9H_2O)$ may be provided as the second material.

The mixed material may further include a noble metal catalyst. For example, Pt, Pd, Au, or Rh may be provided as the noble metal catalyst.

According to an embodiment, the forming of the hollow structure in S10 includes preparing a spray solution in S11, heating spray in S12, and performing heat treatment in S13.

According to an embodiment, in the preparing of the spray solution in S11, the mixed material is dissolved in distilled water to prepare the spray solution.

In the heating of spray in S12, the spray solution prepared in the forming of the spray solution in S11 is sprayed and the sprayed spray solution is heated to form a $CoCr_2O_4$ precursor.

In the performing of the heat treatment in S13, the $CoCr_2O_4$ precursor prepared in the heating of spray in S12 is heat-treated.

In the performing of the coating in S14, the $CoCr_2O_4$ hollow structure prepared in the forming of the hollow structure in S10 is coated on the insulator substrate 200 where the electrodes 301 and 302 are provided.

Hereinafter, detailed Examples manufacturing gas sensors using the above-described method of manufacturing the gas sensor and effects of the gas sensors manufactured according to each embodiment will be described.

Example 1-1

According to Example 1-1, in the preparing the spray solution in S11, a molar ratio of Cr/Co was calculated to be 2.0 in distilled water of 200 mL and cobalt (II) nitrate hexahydrate $[Co(NO_3)_2 \cdot 6H_2O$, 99.999%, Sigma-Aldrich, US] of 1.5 g, chromium (III) nitrate nonahydrate $[Cr(NO_3)_3 \cdot 9H_2O$, 99%, Sigma-Aldrich, US] of 4.1 g, and citric acid $[C_6H_8O_7$, 99.5%, Sigma-Aldrich, USA] of 4.2 g were mixed and stirred until all the reagents are dissolved to prepare the spray solution.

In the heating of the spray in S12, the spray solution prepared in the preparing the spray solution in S11 was ultrasonically sprayed in air at a flow rate of 10 L min$^{-1}$ and simultaneously passed through an electric furnace (600° C.) connected to a spray outlet to form the pure $CoCr_2O_4$ hollow structure precursor.

In the performing of the heat treatment in S13, the $CoCr_2O_4$ precursor formed in the heating of the spray in S12 was heat-treated for 2 hours at 700° C. to form the $CoCr_2O_4$ hollow structure having the hollow shape.

In the performing of the coating step in S14, fine powders of the $CoCr_2O_4$ hollow structure in the performing of the heat treatment in S13 were mixed with distilled water, were dropped onto an alumina $(Al_2O_3)$ substrate in which an Au electrode was formed to be coated, and performed the heat treatment at 450° C. for 2 hours to manufacture the gas sensor.

A method of measuring gas sensitivity of the manufactured gas sensor is as follows.

The manufactured gas sensor was placed inside a gas sensing chamber having a quartz tube, pure air or mixed gas was alternately injected, and the resistance change of the gas sensor was measured in real time. Gases were mixed at an appropriate concentration in advance through a mass flow controller (MFC), and then rapidly injected using a 4-way valve to change the gas concentration inside the gas sensing chamber. The total flow rate inside the gas sensing chamber was fixed at 200 SCCM to maintain a temperature of the gas sensor in spite of a sudden change in gas concentration.

Example 1-21

According to Example 1-2, in the preparing of the spray solution in S11, a molar ratio of Cr/Co was calculated to be 3.0 in distilled water of 200 mL to synthesize the $CoCr_2O_4$ hollow structure with preparing $Cr_2O_3$ and cobalt (II) nitrate hexahydrate of 1.5 g, chromium (III) nitrate nonahydrate of 6.1 g, and citric acid of 4.2 g were mixed and stirred until all the reagents are dissolved to prepare the spray solution.

Thereafter, the method of manufacturing the gas sensor and the method of measuring the gas sensitivity were the same as in Example 1-1.

Example 1-31

According to Example 1-3, in the preparing of the spray solution in S11, a molar ratio of Cr/Co was calculated to be 4.0 higher than Example 1-2 in distilled water of 200 mL and cobalt (II) nitrate hexahydrate of 1.5 g, chromium (III) nitrate nonahydrate of 8.2 g, and citric acid of 4.2 g were mixed and stirred until all the reagents are dissolved to prepare the spray solution.

Thereafter, the method of manufacturing the gas sensor and the method of measuring the gas sensitivity were the same as in Example 1-1.

Example 2-11

According to Example 2-1, in the preparing of the spray solution in S11, a molar ratio of Cr/Co was calculated to be 2.0 in distilled water of 200 mL and cobalt (II) nitrate hexahydrate of 0.38 g, chromium (III) nitrate nonahydrate of 1.02 g, and citric acid of 1.0 g were mixed and stirred until all the reagents are dissolved to prepare the spray solution.

Thereafter, the method of manufacturing the gas sensor and the method of measuring the gas sensitivity were the same as in Example 1-1.

Example 2-2

According to Example 2-2, in the preparing of the spray solution in S11, a molar ratio of Cr/Co was calculated to be 2.0 in distilled water of 200 mL to synthesize Pt-added $CoCr_2O_4$ hollow structure and cobalt (II) nitrate hexahydrate of 0.38 g, chromium (III) nitrate nonahydrate of 1.02 g, chloroplatinic acid solution (8 wt % in $H_2O$, $H_2PtCl_6$, Sigma-Aldrich, USA) of 0.05 mL, and citric acid of 1.0 g were mixed and stirred until all the reagents are dissolved to prepare the spray solution.

Thereafter, the method of manufacturing the gas sensor and the method of measuring the gas sensitivity were the same as in Example 1-1.

Example 2-3

According to Example 2-3, in the preparing of the spray solution in S11, a molar ratio of Cr/Co was calculated to be 2.0 in distilled water of 200 mL to synthesize Pd-added $CoCr_2O_4$ hollow structure and cobalt (II) nitrate hexahydrate of 0.38 g, chromium (III) nitrate nonahydrate of 1.02 g, palladium nitrate hydrate ($Pd(NO_3)_2 \cdot xH_2O$, Sigma-Aldrich, USA) of 0.0014 g, and citric acid of 1.0 g were mixed and stirred until all the reagents are dissolved to prepare the spray solution.

Thereafter, the method of manufacturing the gas sensor and the method of measuring the gas sensitivity were the same as in Example 1-1.

Example 2-4

According to Example 2-4, in the preparing of the spray solution in S11, a molar ratio of Cr/Co was calculated to be 2.0 in distilled water of 200 mL to synthesize Au-added $CoCr_2O_4$ hollow structure and cobalt (II) nitrate hexahydrate of 0.38 g, chromium (III) nitrate nonahydrate of 1.02 g, gold chloride trihydrate ($HAuCl_4 \cdot 3H_2O$, Sigma-Aldrich, USA) of 0.0012 g, and citric acid of 1.0 g were mixed and stirred until all the reagents are dissolved to prepare the spray solution.

Thereafter, the method of manufacturing the gas sensor and the method of measuring the gas sensitivity were the same as in Example 1-1.

The gas sensors were prepared using the fine powders synthesized in the above Examples and Comparative Examples and were measured at various temperatures, to exhibit p-type semiconductor type characteristics in which resistances were increased for all measured reducing gases. Therefore, gas sensitivity was defined as $R_g R_a^{-1}$ ($R_g$: device resistance in gas, $R_a$: device resistance in air). The gas sensors were manufactured using the synthesized fine powders, and then the gas sensitivity was measured, and the selectivity was calculated based on the difference in sensitivity from other gases.

When the resistance of each sensor stabilized in the air, the atmosphere was changed to test gas (ethanol, xylene, toluene, benzene, formaldehyde, trimethylamine, ammonia, carbon monoxide each of 5 ppm), and when the resistance in the test gas was constant, the atmosphere was changed back to the air to measure the resistance change. A final resistance reached when exposed to the test gas was defined as $R_g$ and a resistance in the air was defined as $R_a$. The xylene selectivity measured by each gas sensor was calculated from a ratio ($S_X/S_E$) of xylene sensitivity "$S_X$" to ethanol sensitivity $S_E$". Here, ethanol is the hindered gas.

Figure 3:
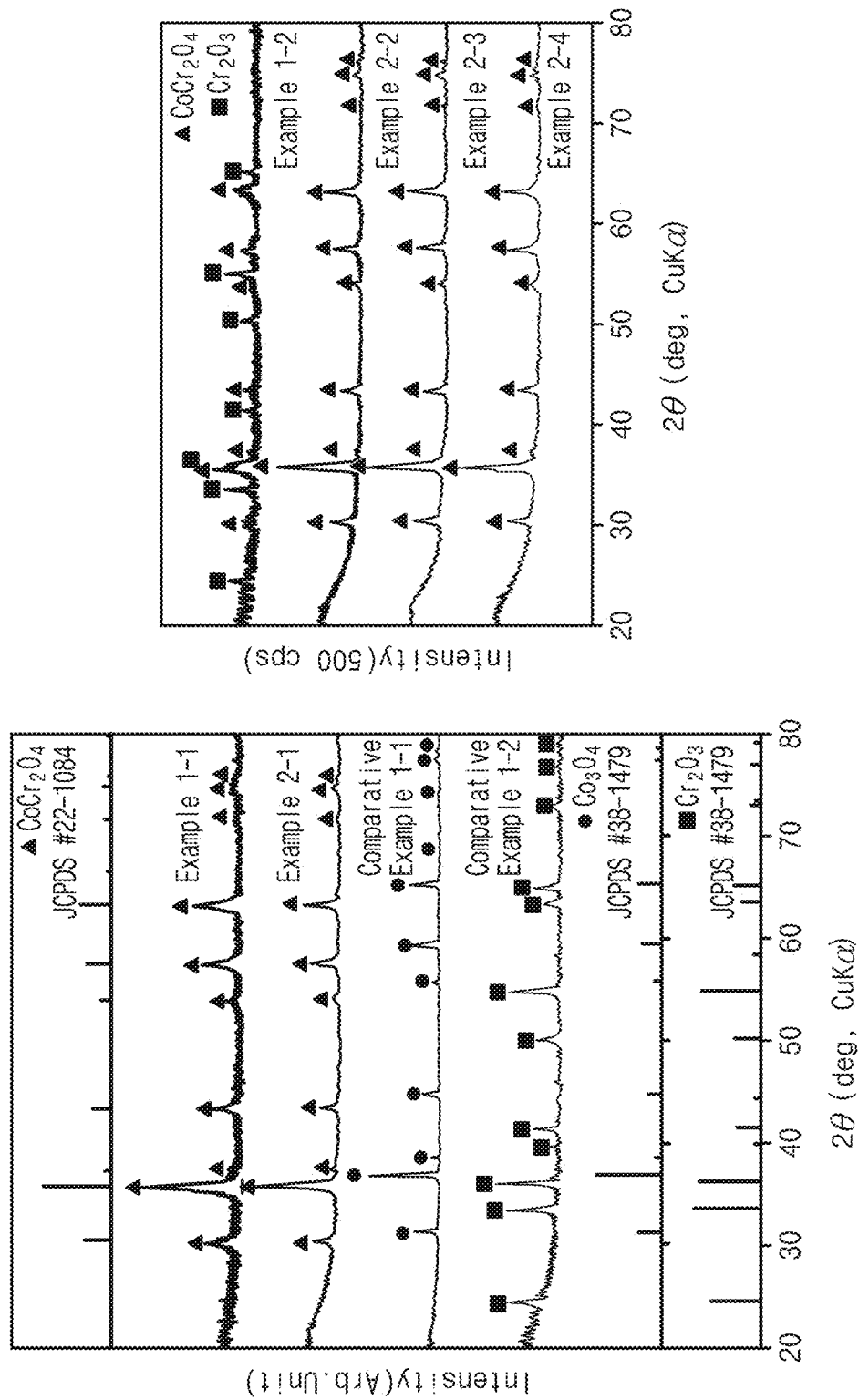
FIG. 3 is a graph illustrating results of X-ray diffraction analysis of Examples 1-1, 1-2, 2-1, 2-2, 2-3, and 2-4 and Comparative Examples 1-1 and 1-2.

FIG. 3 is a graph illustrating results of X-ray diffraction analysis of Examples 1-1, 1-2, 2-1, 2-2, 2-3, and 2-4 and Comparative Examples 1-1 and 1-2. Referring to FIG. 3, it was confirmed that Example 1-1 and Example 2-1 included $CoCr_2O_4$ without $Co_3O_4$ or $Cr_2O_3$ diffraction patterns through the results of the X-ray diffraction analysis, same as Comparative Examples 1-1 and 1-2. It was confirmed that Example 1-2 had a pattern of a nanocomposite in which $Cr_2O_3$ and $CoCr_2O_4$ are mixed at a specific ratio and Examples 2-2, 2-3, and 2-4 showed $CoCr_2O_4$ diffraction patterns. The diffraction patterns of the noble metal catalysts (Pt, Pd, and Au) in Examples 2-2, 2-3 and 2-4 were not confirmed due to detection limit of the X-ray diffraction analysis.

Figure 4:
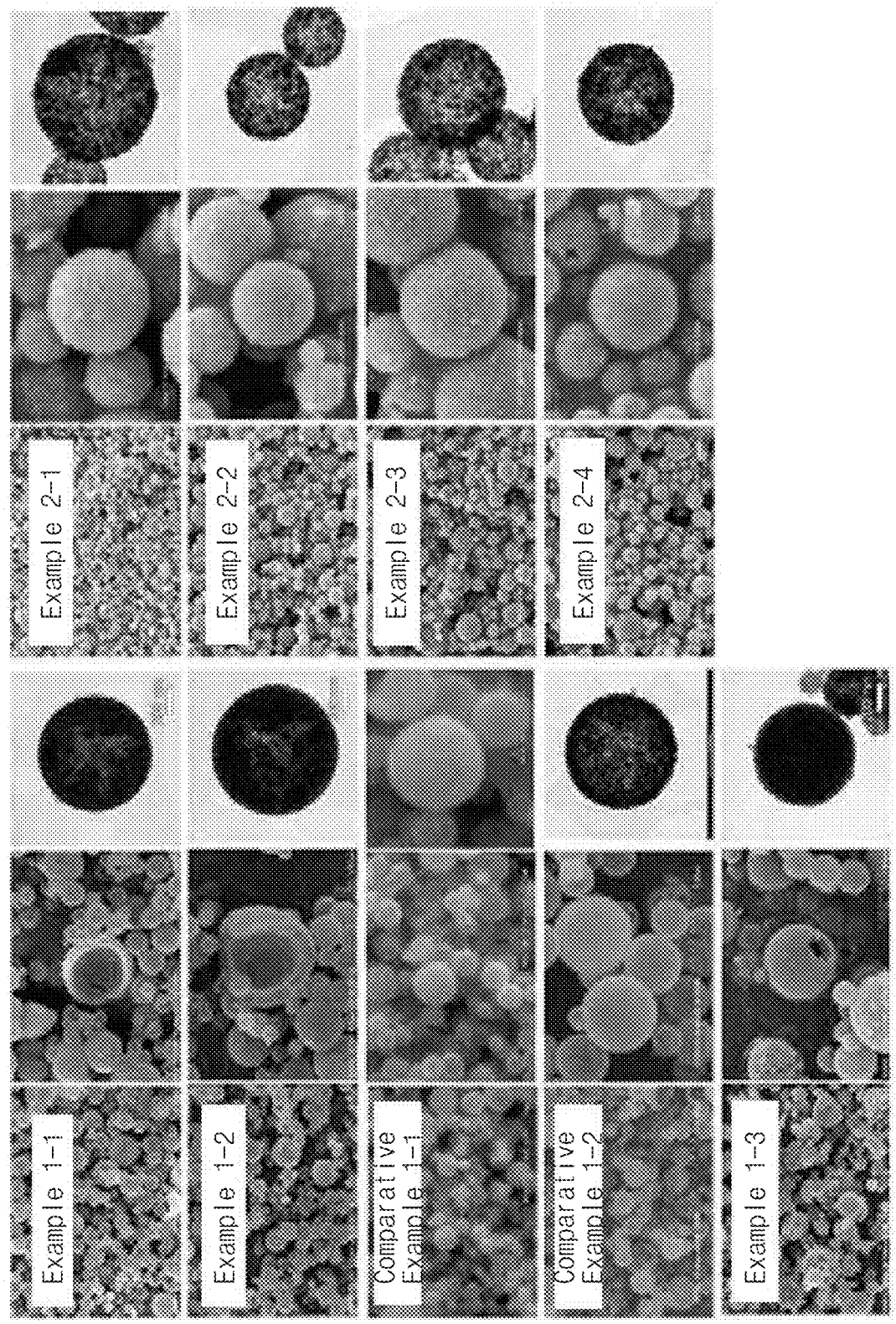
FIG. 4 is SEM and TEM pictures taken secondary particle structures of fine powders prepared in each Example and each Comparative Example.

FIG. 4 is SEM and TEM pictures taken secondary particle structures of fine powders prepared in each Example and each Comparative Example. Referring to FIG. 4, it was confirmed that the particles prepared in all Examples and Comparative Examples had a spherical hollow structure.

Figure 5:
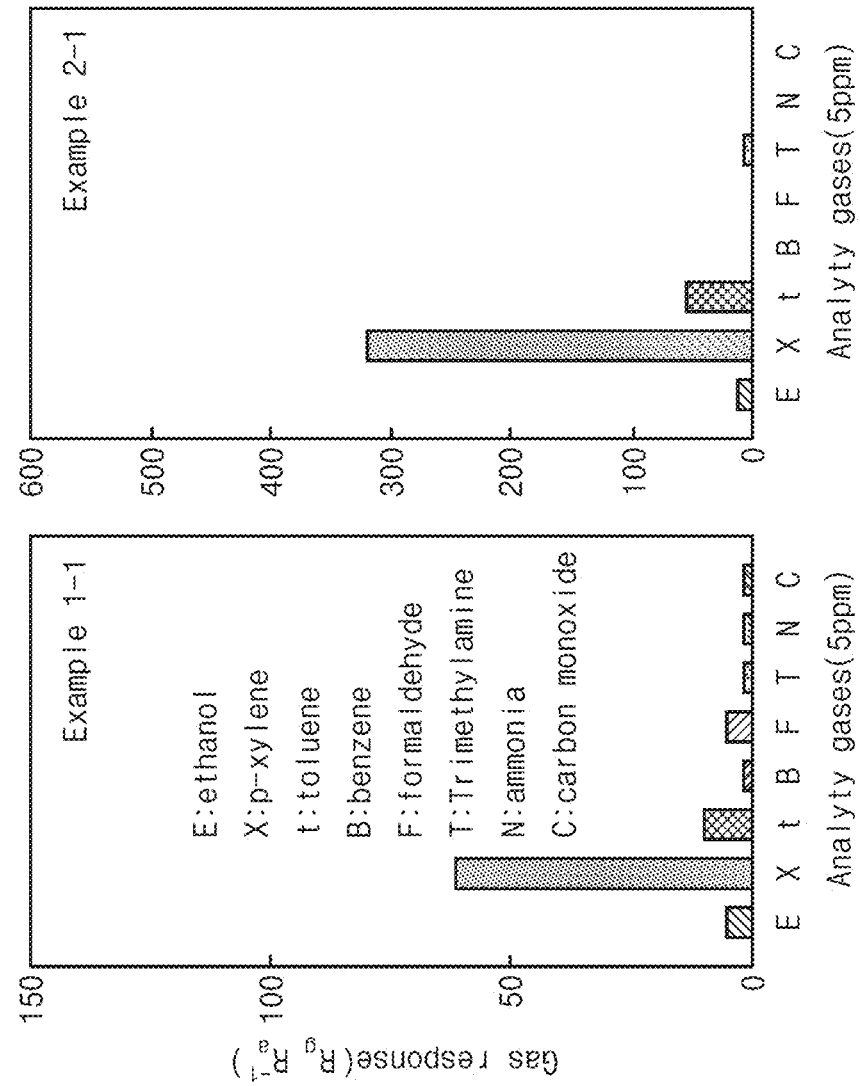
FIG. 5 is a graph illustrating gas sensitivity to ethanol, xylene, toluene, benzene, formaldehyde, trimethylamine, ammonia and carbon monoxide, each which had 5 ppm concentration at an operating temperature of 275° C. in Example 1-1 and Example 2-1, Comparative Example 1-1, and Comparative Example 1-2.
Figure 5:
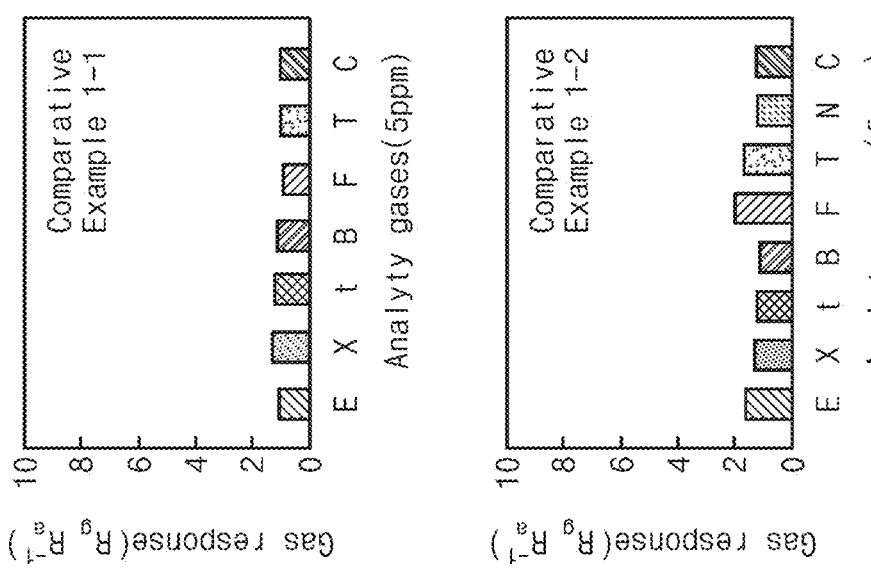

FIG. 5 is a graph illustrating gas sensitivity to ethanol, xylene, toluene, benzene, formaldehyde, trimethylamine, ammonia and carbon monoxide, each which had 5 ppm concentration at an operating temperature of 275° C. in Example 1-1, Example 2-1, Comparative Example 1-1, and Comparative Example 1-2. Referring to FIG. 5, Comparative Examples 1-1 and 1-2, which were hollow structures synthesized only with $Co_3O_4$ and $Cr_2O_3$ respectively, were confirmed to have little sensitivity to the above-described gases. It was confirmed that pure $CoCr_2O_4$ showed excellent sensitivity to xylene ($S_X$=61.4) through evaluation of gas sensitivity characteristics of Example 1-1. In addition, it was confirmed that the gas sensitivity of Example 2-1, which was pure $CoCr_2O_4$ having a thin shell by reducing addition amounts of Co and Cr, was greatly increased ($S_X$=319.5). This showed that $CoCr_2O_4$ exhibited high sensitivity and selectivity to xylene, regardless of its structure, and the sensitive material having the thin shell rapidly spreads the gas introduced into the gas sensitive material to the gas sensitive material inside, thereby increasing the gas sensitivity.

Figure 6:
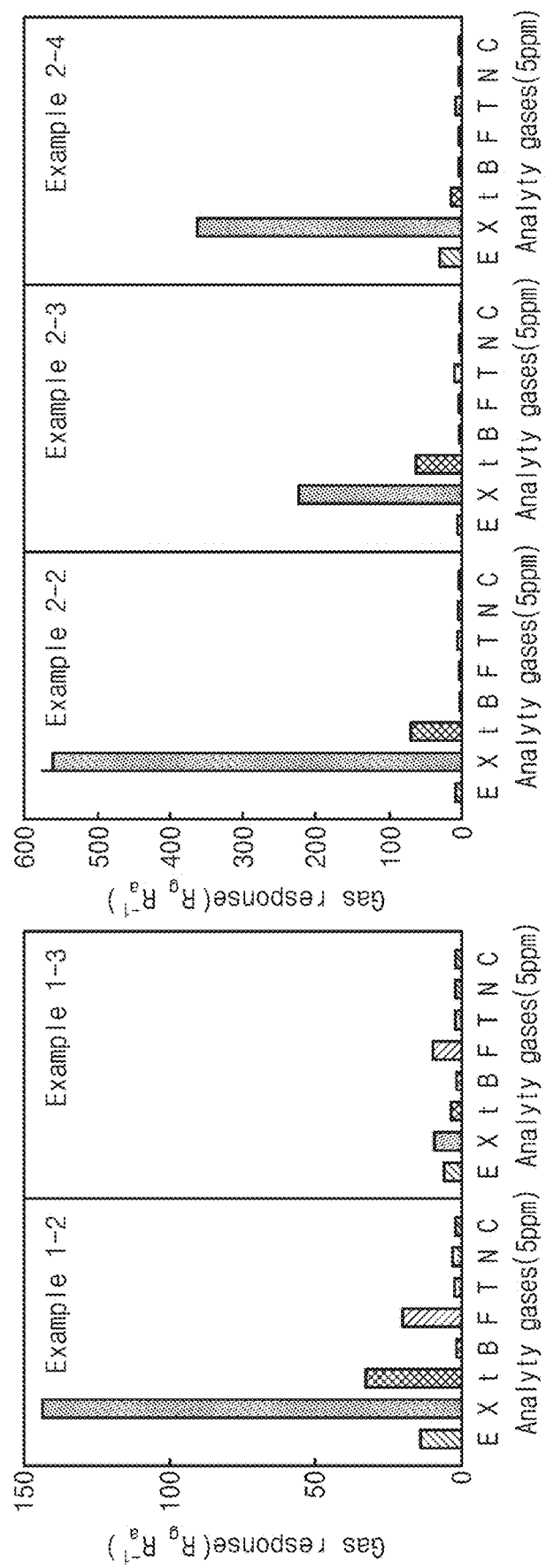
FIG. 6 is a graph illustrating gas sensitivity for ethanol, xylene, toluene, benzene, formaldehyde, trimethylamine, ammonia and carbon monoxide, each which had 5 ppm concentration at an operating temperature of 275° C. in gas sensors manufactured by Examples 1-2, 1-3, 2-2, 2-3, 2-4.

FIG. 6 is a graph illustrating gas sensitivity for ethanol, xylene, toluene, benzene, formaldehyde, trimethylamine, ammonia and carbon monoxide, each which had 5 ppm concentration at an operating temperature of 275° C. in gas sensors manufactured by Examples 1-2, 1-3, 2-2, 2-3, and 2-4. Referring to FIG. 6, it was confirmed that the sensitivity to xylene increased when a specific amount of $Cr_2O_3$ secondary phase was generated through Examples 1-2 and 1-3 but when the $Cr_2O_3$ secondary phase was excessively generated, the gas sensitivity was low for all gases. Therefore, it could be predicted that the gas sensitivity was low for all gases when the molar ratio of Cr/Co was 4.0 or more. The xylene sensitivity of Example 1-2 was greater than the xylene sensitivity of Example 1-1. This was because transfer of charge between two p-type semiconductors having different work functions occurs to generate electrical sensitization of the $CoCr_2O_4$ sensitive material when the CrC2O4 phase was predominant and $Cr_2O_3$ was discontinuously added. Furthermore, the addition of the noble metal catalysts Pt and Au through Examples 2-2 and 2-4 greatly increased the xylene sensitivity. However, it was thought that the addition of Au also increased the sensitivity of ethanol, i.e., the hindered gas, by the electronic sensitization to have the xylene selectivity slightly lower than that of the addition of Pt. It was shown that Pd-added $CoCr_2O_4$ of Example 2-3 had the xylene sensitivity ($S_X$=225.8) lower than that of pure $CoCr_2O_4$ ($S_X$=319.5). It was thought to be due to oxidation of xylene at an upper end of a sensor sensitive layer by catalytic activity of Pd, which was known as an oxidation catalyst for methylbenzene, such as xylene and toluene, and $CoCr_2O_4$. Therefore, it could be confirmed that the Pt catalyst served as greatly improving the sensitivity and selectivity to xylene in the $CoCr_2O_4$ sensor.

Figure 7:
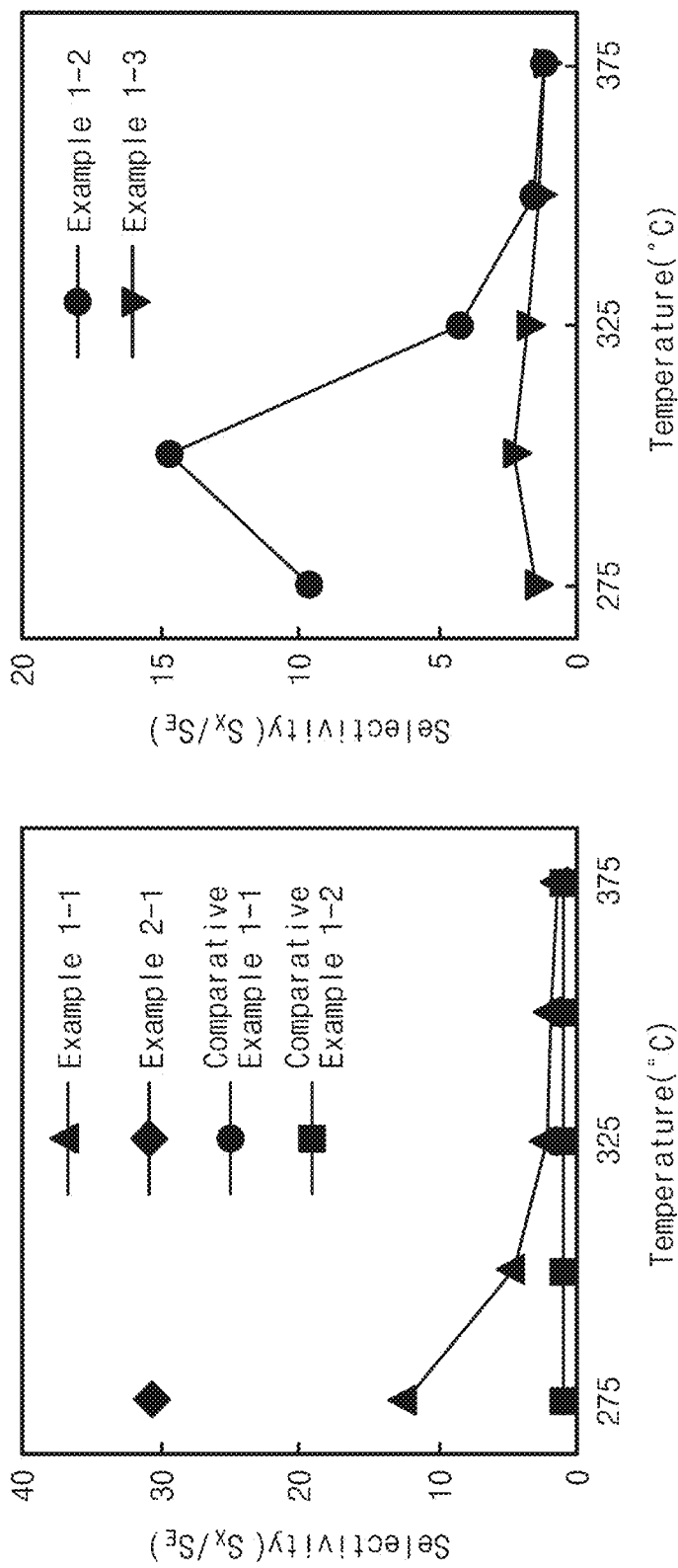
FIG. 7 is a graph illustrating changes of sensitivity ratios of xylene sensitivity to ethanol sensitivity of gas sensors manufactured in Examples 1-1, 1-2, 1-3, and 2-1 and Comparative Examples 1-1 and 1-2 with temperature.

FIG. 7 is a graph illustrating changes of sensitivity ratios of xylene sensitivity to ethanol sensitivity of gas sensors manufactured in Examples 1-1, 1-2, 1-3, and 2-1 and Comparative Examples 1-1 and 1-2 with temperature. Referring to FIG. 7, Comparative Example 1-1 and Comparative Example 1-2 were shown that it was impossible to selectively detect xylene using $Co_3O_4$ and $Cr_2O_3$ because the selectivity ($S_X/S_E$) of the gas sensor with respect to xylene had a value within 1 at all temperatures. Example 1-1 and Example 2-1 showed values of $S_X/S_E$=12.3 and 30.7 at 275° C., respectively and the possibility of highly selective detection of xylene with $CoCr_2O_4$ alone. It was shown that the sensitivity to xylene gas increased to increase the selectivity of xylene when a certain amount of $Cr_2O_3$ secondary phase was generated through Example 1-2. Furthermore, it was confirmed that, when the amount of $Cr_2O_3$ secondary phase excessively increased (Examples 1-3, the molar ratio of Cr/Cr was 4.0), the low xylene selectivity similar to Comparative Example 1-2 i.e., pure $Cr_2O_3$, was exhibited because the gas sensitivity occurred mainly through $Cr_2O_3$ having a low sensitivity. The above results showed that in order to detect xylene gas with high sensitivity and high selectivity, it was preferable that $CoCr_{2O4}$ phase was predominant and $Cr_2O_3$ was discontinuously added. In this embodiment, the results were shown that the most appropriate concentration ratio of Cr/Co was 3.0. This was thought to reduce the sensitivity to xylene and all hindered gases when $Cr_2O_3$ was added in excess. In addition, it could be confirmed that the selectivity to xylene was lowered at 350° C. or more. Furthermore, it was thought that the gas sensor according to an embodiment of the inventive concept was capable of having the selectivity to xylene in a temperature range of 250° C. to 350° C. considering that the oxide semiconductor gas sensor was capable of detecting the gas at a temperature higher than 250° C., normally.

Figure 8:
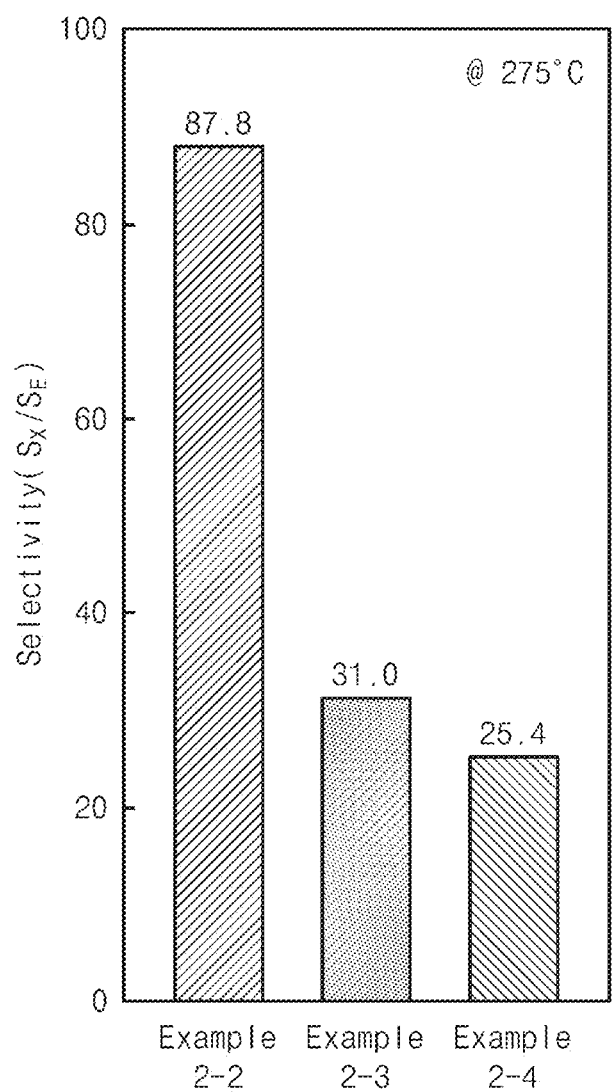
FIG. 8 is a graph illustrating selectivity ($S_X/S_E$) of xylene in Example 2-2, Example 2-3, and Example 2-4 at an operating temperature 275° C.

FIG. 8 is a graph illustrating selectivity ($S_X/S_E$) of xylene in Example 2-2, Example 2-3, and Example 2-4 at an operating temperature 275° C. Referring to FIG. 8, the xylene selectivity ($S_X/S_E$) of Examples 2-2, 2-3, and 2-4 was confirmed at the gas sensor operating temperature of 275° C. As a result of measurement, it was confirmed that Example 2-2 had a very good selectivity of xylene to ethanol ($S_X/S_E$=87.8). Due to the addition of Pt known as an ethanol oxidation catalyst, ethanol was all oxidized at the upper end of the sensor sensitive layer but all xylene was not decomposed at the upper end of the sensitive layer to diffuse to a lower end of the sensitive layer. It was thought that as xylene diffused into the sensitive material, was converted into a highly reactive gas by Pt and $CoCr_2O_4$, and promoted a gas sensitive reaction, the addition of Pt decreased the sensitivity of ethanol and greatly increased the sensitivity of xylene to have high sensitivity and selectivity to xylene. On the other hand, the xylene selectivity ($S_X/S_E$=31.0) of Example 2-3 having Pd-add $CoCr_2O_4$ and the xylene selectivity ($S_X/S_E$=25.4) of Example 2-4 having Au-add $CoCr_2O_4$ showed similar or lower values to the xylene selectivity of Example 2-1 having pure $CoCr_2O_4$. It was shown that in Pd-add $CoCr_2O_4$, ethanol and some xylene were oxidized and decomposed in the upper end of the sensor sensitive layer by excessively high catalytic activity of Pd, to decrease both sensitivity of xylene and ethanol similar to the xylene selectivity of pure $CoCr_2O_4$. It was shown that in Au-add $CoCr_2O_4$, the sensitivity of the gases was all increased by the electrical sensitization, but the sensitivity to ethanol was highly increased and the xylene selectivity was low compared to pure $CoCr_2O_4$.

Figure 9:
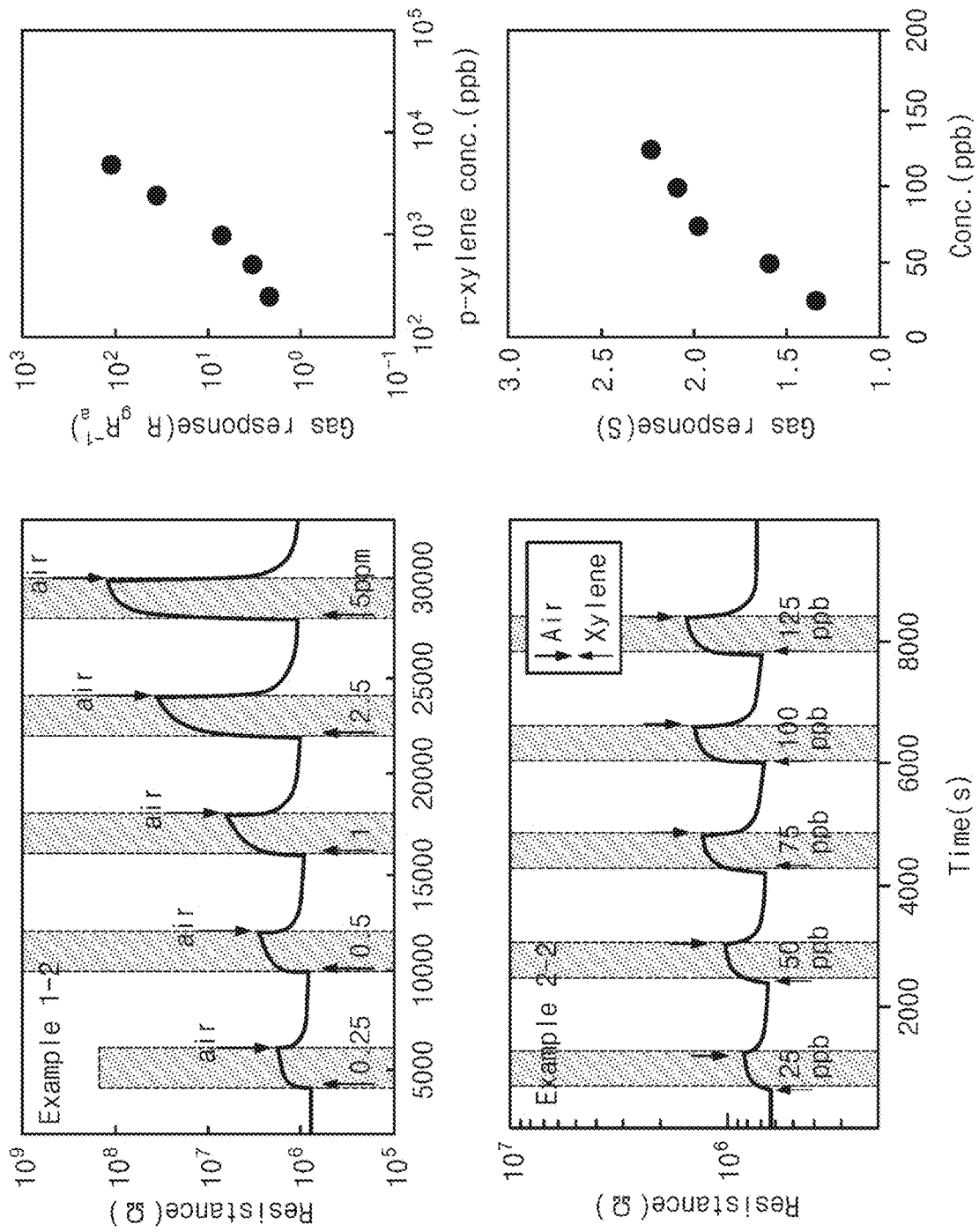
FIG. 9 is a graph illustrating sensitivity characteristics of xylene gas in Example 1-2 (300° C.) and Example 2-2 (275° C.) at sensor operating temperatures showing the highest selectivity with respect to changes of gas concentration.

FIG. 9 is a graph illustrating sensitivity characteristics of xylene gas in Example 1-2 (300° C.) and Example 2-2 (275° C.) at sensor operating temperatures showing the highest selectivity with respect to changes of gas concentration. Referring to FIG. 9, it was confirmed that Example 1-2 showed xylene sensitivity values of 2.19, 3.28, 6.70, 34.65 and 109.5 to xylene concentrations of 0.25, 0.5, 1, 2.5 and 5 ppm, respectively, at the operating temperature of 300° C. This was a result showing that Example 1-2 was an excellent gas sensor which was capable of being measured with high sensitivity of xylene at a concentration level of 250 ppb. In addition, it was confirmed that Example 2-2 showed xylene sensitivity values of 1.33, 1.58, 1.97, 2.08, and 2.22 to xylene concentrations of 25, 50, 75, 100, and 125 ppb, respectively, at the operating temperature of 275° C. It was shown that the sensor of Example 2-2 was capable of measuring trace amounts of xylene at the level of 10 ppb. Therefore, the gas sensor according to an embodiment of the inventive concept is capable of measuring the concentration of the trace amount of xylene and a change amount of xylene in real time.

Figure 10:
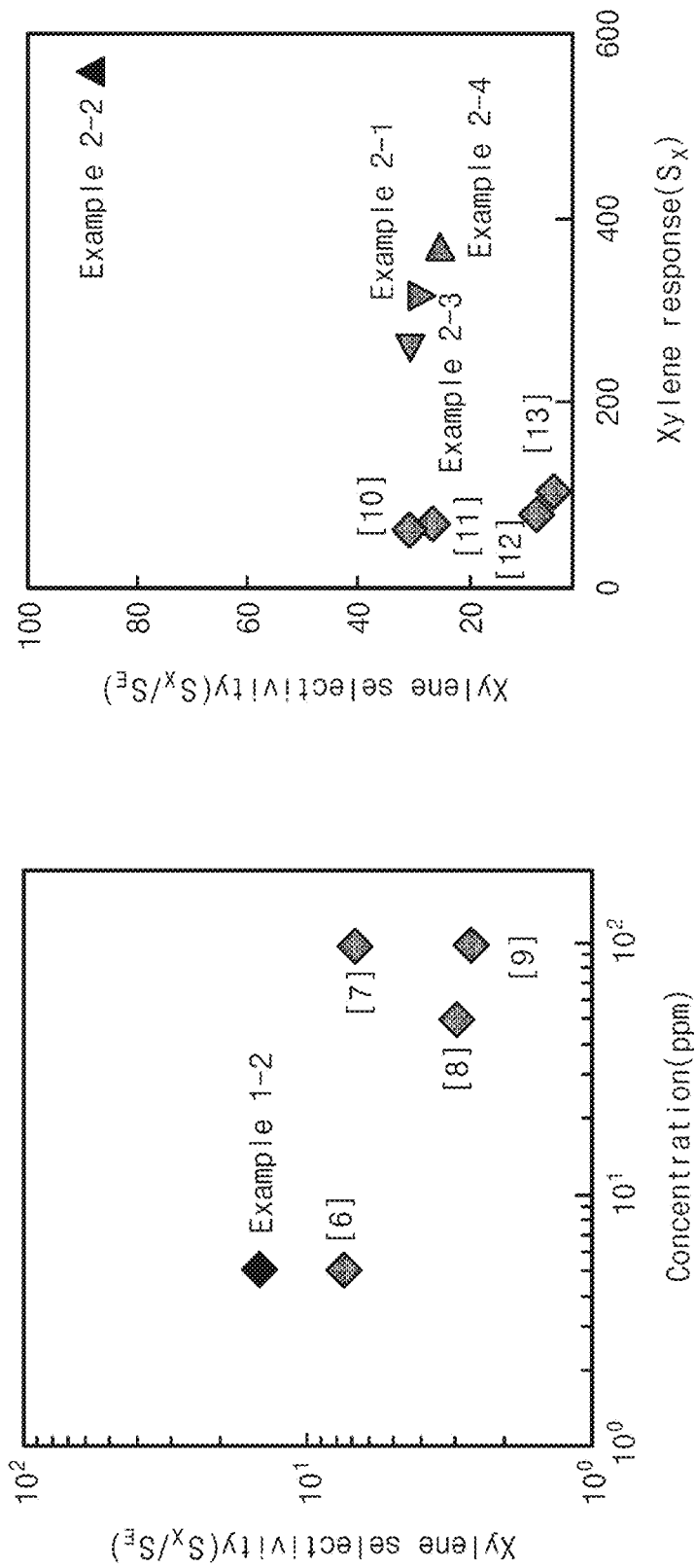
FIG. 10 is a graph illustrating results of comparing xylene sensitivity for each concentration with the existing studies.

FIG. 10 is a graph illustrating results of comparing xylene sensitivity for each concentration with the existing studies. Referring to FIG. 10, it was confirmed that each xylene sensitivity of Examples 1-2 and 2-1 of the inventive concept was much higher than that of studies (6, 7, 8, 9, 10, 11, 12, 13) previously conducted. In particular, it was shown that the sensitivity and selectivity to xylene in Example 2-2 were significantly superior to the existing results (10, 11, 12, 13). In addition, it was confirmed that low concentration of xylene was capable of being effectively detected compared with NiO, $Co_3O_4$ and the like, which were generally known to have high methylbenzene sensitivity. A conventional oxide semiconductor-based xylene sensor had very poor sensitivity and selectivity and was difficult to measure only xylene, while the sensor of the inventive concept may measure extremely small amounts of xylene with high sensitivity and high selectivity.

Figure 11:
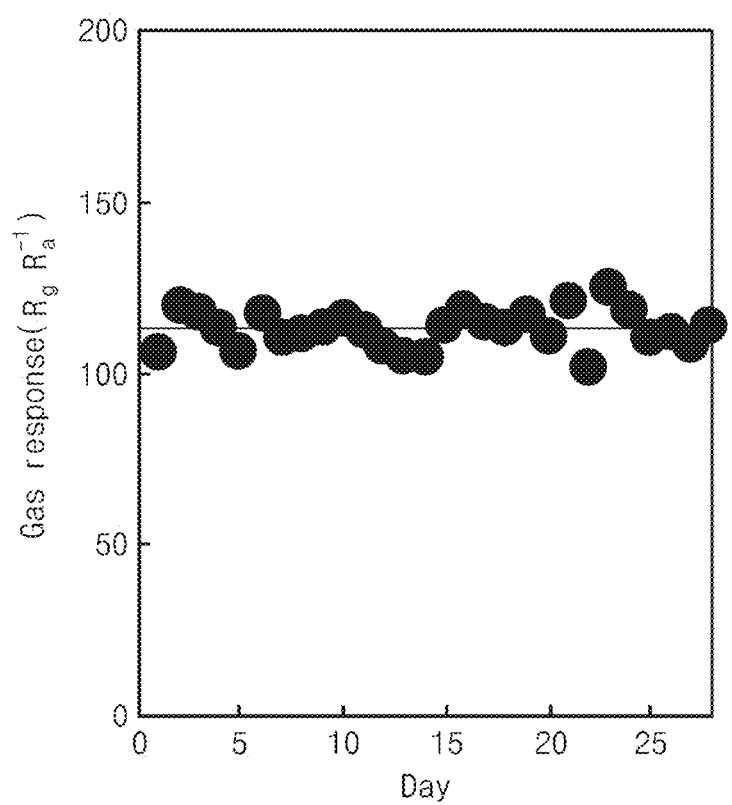
FIG. 11 is a graph showing results of measuring gas sensitivity ($R_g\ R_a^{-1}$) of Example 1-2 of the inventive concept for 30 days.

FIG. 11 is a graph showing results of measuring gas sensitivity ($R_g R_a^{-1}$) of Example 1-2 of the inventive concept for 30 days. Referring to FIG. 11, it was confirmed that the gas sensor according to an embodiment of the inventive concept was capable of maintaining stable gas sensitivity for at least 30 days.

The gas sensor according to an embodiment of the inventive concept may have a high selectivity and high sensitivity to xylene.

The above detailed description illustrates the inventive concept. In addition, the above-mentioned contents show and explain preferred embodiments of the inventive concept and the inventive concept may be used in various other combinations, modifications, and environments. That is, changes or modifications may be made within the scope of the concept of the inventive concept disclosed in the present specification, the scope equivalent to the disclosures described above, and/or the skill or knowledge in the art. The described embodiments illustrate the best state for implementing the technical idea of the inventive concept and various modifications required in the specific application field and use of the inventive concept are possible. Thus, the detailed description of the inventive concept is not intended to limit the inventive concept to the disclosed embodiments. Also, the appended claims should be construed to include other embodiments.

What is claimed is:

1. A gas sensor comprising:
a gas sensing layer capable of reacting with xylene,
wherein the gas sensing layer consisting of a $CoCr_2O_4$ hollow structure and a noble metal catalyst selected from the group consisting of Pt, Au, and Rh.

2. The gas sensor of claim 1, further comprising:
an insulator substrate formed of an insulator material; and
an electrode connected to the insulator substrate,
wherein the gas sensing layer is coated on the insulator substrate, and
wherein the electrode is connected between the insulator substrate and the gas sensing layer.

3. The gas sensor of claim 1, further comprising:
a heater heating the gas sensing layer.

* * * * *